US012734188B2

(12) United States Patent
Singh et al.

(10) Patent No.: US 12,734,188 B2
(45) Date of Patent: Sep. 15, 2026

(54) PHARMACEUTICAL COMPOSITION COMPRISING COMBINATION OF SITAGLIPTIN AND EMPAGLIFLOZIN

(71) Applicant: UNISON PHARMACEUTICALS PVT. LTD., Ahmedabad (IN)

(72) Inventors: Balvir Singh, Ahmedabad (IN); Ramesh Shingala, Ahmedabad (IN); Milap Patel, Gandhinagar (IN); Ritesh Patel, Ahmedabad (IN)

(73) Assignee: UNISON PHARMACEUTICALS PVT. LTD., Ahmedabad (IN)

( * ) Notice: Subject to any disclaimer, the term of this patent is extended or adjusted under 35 U.S.C. 154(b) by 237 days.

(21) Appl. No.: 18/580,779

(22) PCT Filed: Oct. 10, 2022

(86) PCT No.: PCT/IN2022/050908
§ 371 (c)(1),
(2) Date: Jan. 19, 2024

(87) PCT Pub. No.: WO2023/062648
PCT Pub. Date: Apr. 20, 2023

(65) Prior Publication Data

US 2024/0374627 A1 Nov. 14, 2024

(30) Foreign Application Priority Data

Oct. 12, 2021 (IN) ............................ 202121046486

(51) Int. Cl.

| | |
|---|---|
| ***A61K 31/7048*** | (2006.01) |
| ***A61K 9/20*** | (2006.01) |
| ***A61K 9/24*** | (2006.01) |
| ***A61K 31/4985*** | (2006.01) |
| ***A61K 47/18*** | (2017.01) |

(52) U.S. Cl.
CPC ........ *A61K 31/7048* (2013.01); *A61K 9/2009* (2013.01); *A61K 9/2018* (2013.01); *A61K 9/2054* (2013.01); *A61K 9/209* (2013.01); *A61K 31/4985* (2013.01); *A61K 47/183* (2013.01)

(58) Field of Classification Search
CPC .............. A61K 31/7048; A61K 9/2009; A61K 9/2018; A61K 9/2054; A61K 9/209; A61K 31/4985; A61K 47/183
See application file for complete search history.

(56) References Cited

U.S. PATENT DOCUMENTS

| | | | |
|---|---|---|---|
| 6,414,126 | B1 | 7/2002 | Ellsworth et al. |
| 7,407,955 | B2 | 8/2008 | Himmelsbach et al. |
| 7,515,117 | B2 | 4/2009 | Moon |
| 8,221,786 | B2 | 7/2012 | Bindra et al. |
| 11,033,552 | B2 | 6/2021 | Kohlrausch et al. |
| 2011/0098240 | A1 | 4/2011 | Dugi et al. |
| 2011/0195917 | A1 | 8/2011 | Dugi et al. |
| 2012/0071403 | A1 | 3/2012 | Strumph et al. |
| 2013/0224296 | A1 | 8/2013 | Narang et al. |
| 2014/0079778 | A1 | 3/2014 | Narang et al. |
| 2015/0283248 | A1 | 10/2015 | Jayaramareddy et al. |
| 2017/0319539 | A1 | 11/2017 | Jetti et al. |
| 2018/0243310 | A1 | 8/2018 | Krekeler |
| 2019/0110994 | A1 | 4/2019 | Shervi et al. |
| 2021/0260084 | A1 | 8/2021 | Shah et al. |

FOREIGN PATENT DOCUMENTS

| | | | |
|---|---|---|---|
| CN | 109549939 | A | 4/2019 |
| CN | 112716966 | A | 4/2021 |
| IN | 201721036839 | | 4/2019 |
| IN | 201741023337 | | 4/2019 |
| KR | 20190040765 | A | 4/2019 |
| WO | WO 2008/002824 | A1 | 1/2008 |
| WO | WO 2009/022008 | A1 | 2/2009 |
| WO | WO 2009/022009 | A1 | 2/2009 |
| WO | WO 2009/022010 | A1 | 2/2009 |

(Continued)

OTHER PUBLICATIONS

Lobmann et al. (Amino acids as co-amorphous stabilizers for poorly water soluble drugs—Part 1: Preparation, stability and dissolution enhancement), European Journal of Pharmaceutics and Biopharmaceutics 85 (2013) 873-881.*

U.S. Appl. No. 18/580,748, filed Jan. 19, 2024.

Abdel-Ghany et al., "Pharmaceutical Analysis of Linagliptin and Empagliflozin using LC-MS/MS." *Der Pharma Chemica*, 8(17): 186-189 (2016).

Abdul-Ghani, "Where Does Comination Therapy With an SGLT2 Inhibitor Plus a DPP-4 Inhibitor Fit in the Management of Type 2 Diabetes?", *Diabetes Care*, vol. 38, pp. 373-375 (2015).

Al Ameri et al., "The Implications of Fixed Dose Combination (FDC) Compared to Single Pill Combinations (SPC): Based on Patients' View." *International Journal of Pharmacy*, 8(1): 127-136 (2018).

(Continued)

*Primary Examiner* — Zohreh A Fay
(74) *Attorney, Agent, or Firm* — Leydig, Voit & Mayer, Ltd.

(57) ABSTRACT

The present invention relates to a stable pharmaceutical composition comprising a fixed dose combination of a therapeutically effective amount of DPP-IV inhibitor and a therapeutically effective amount of SGLT2 inhibitor for reducing blood glucose level in patients with diabetes. The present invention specifically relates to a stable pharmaceutical composition comprising Sitagliptin or a pharmaceutically acceptable salts or solvate or hydrate or premix thereof and Empagliflozin or a pharmaceutically acceptable salt or solvate or hydrate or premix thereof in the presence of one or more pharmaceutically acceptable excipients. Moreover, the present invention relates to a stable pharmaceutical composition comprising Sitagliptin Phosphate Monohydrate, Empagliflozin and one or more pharmaceutically acceptable excipients with high content uniformity, reduced degradation impurities and optimum dissolution.

8 Claims, No Drawings

(56) References Cited

FOREIGN PATENT DOCUMENTS

| | | | | |
|---|---|---|---|---|
| WO | WO 2009/091082 A1 | | 7/2009 | |
| WO | WO 2010/092124 A1 | | 8/2010 | |
| WO | WO 2010/092125 A1 | | 8/2010 | |
| WO | WO 2012/120040 A1 | | 9/2012 | |
| WO | WO 2011/002011 A1 | | 12/2012 | |
| WO | WO 2014/080383 A1 | | 5/2014 | |
| WO | WO 2014/083554 A1 | | 6/2014 | |
| WO | WO 2015/173584 A1 | | 11/2015 | |
| WO | WO 2018/124468 A1 | | 7/2018 | |
| WO | WO 2018/124497 A1 | | 7/2018 | |
| WO | WO 2019/120162 A1 | | 6/2019 | |
| WO | WO 2019/221473 A1 | | 11/2019 | |
| WO | WO 2020/009675 A2 | | 1/2020 | |
| WO | WO 2020/018034 A2 | | 1/2020 | |
| WO | WO 2020/058095 A1 | | 3/2020 | |
| WO | WO 2020/106020 A1 | | 5/2020 | |
| WO | WO 2020/130502 A1 | | 6/2020 | |
| WO | WO 2021/176096 A1 | | 9/2021 | |
| WO | WO-2021218638 A1 | * | 11/2021 | ............ A61K 31/35 |

OTHER PUBLICATIONS

Aronson, "Single-pill combination therapy for type 2 diabetes mellitus: linagliptin plus empagliflozin." *Current Medical Research & Opinion*, 1-37 (2014).

Babu et al., "Novel Stress Indicating RP-HPLC Method Development and Validation for the Simultaneous Estimation of Ertugliflozin and Sitagliptin in Bulk and its Formulation." *Oriental Journal of Chemistry*, 34(5): 2554-2561 (2018).

Basile, "A New Approach to Glucose Control in Type 2 Diabetes: The Role of Kidney Sodium-Glucose Co-transporter 2 Inhibition." *Postgraduate Medicine*, 123(4): 38-45 (Jul. 2011).

Benford et al., "Fixed-Dose Combination Antidiabetic Therapy: Real-World Factors Associated with Prescribing Choices and Relationship with Patient Satisfaction and Compliance." *Advances in Therapy*, 29(1): 26-40 (2012).

Bhole et al., "Stability Indicating HPTLC Method for Simultaneous Estimation of Empagliflozin and Linagliptin in Pharmaceutical Formulation," *Analytical Chemistry Letters*, 7(1): 76-85 (2017).

Boulton et al., "Simultaneous oral therapeutic and intravenous 14C-microdoses to determine the absolute oral bioavailability of saxagliptin and dapagliflozin." *British Journal of Clinical Pharmacology*, 75(3):763-768 (Jul. 2012).

Brand et al., "Pharmacokinetics of Empagliflozin, a Sodium Glucose Cotransporter-2 (SGLT-2), Coadministered with Sitagliptin in Healthy Volunteers" *AdvTher*, 29(10): 889-899 (2012).

Cai et al., "Characteristics of patients prescribed sitagliptin and other oral antihyperglycaemic agents in a large US claims database," *International Journal of Clinical Practice*, 64(12): 1601-1608 (Nov. 2010).

Charokopou et al., "Cost-effectiveness of dapagliflozin versus DPP-4 inhibitors as an add-on to Metformin in the Treatment of Type 2 Diabetes Mellitus from a UK Healthcare System Perspective." *BMC Health Services Research*, 15(496): 1-11 (2015).

Chen et al., "Effects of Combining Linagliptin Treatment with BI-38335, A Novel SGLT2 Inhibitor, on Pancreatic Islet Function and Inflammation in db/db Mice." *Current Molecular Medicine*, 12(8): 995-1004 (2012).

Cholke et al., "Comparative Study of Two Different Marketed Preparation (Tablets) Containing Empagliflozin and Linagliptin and Developing Novel Method for Simultaneous Estimation of Empagliflozin and Linagliptin Using UV Visible Spectrophotometer." *World Journal of Pharmacy and Pharmaceutical Sciences*, 8(4): 1227-1235 (2019).

Coppenrath et al., "Dapagliflozin/Saxagliptin Fixed-Dose Tablets: A New Sodium-Glucose Cotransporter 2 and Dipeptidyl Peptidase 4 Combination for the Treatment of Type 2 Diabetes." *Annals of Pharmacotherapy*, 1-8 (2017).

DeFronzo et al., "Combination of Empagliflozin and Linagliptin as Second-Line Therapy in Subjects With Type 2 Diabetes Inadequately Controlled on Metformin." *Diabetes Care*, 1-10 (2015).

Dey, "SGLT2 inhibitor/DPP-4 inhibitor combination therapy—complementary mechanisms of action for management of type 2 diabetes mellitus," *Postgraduate Medicine*, (Mar. 21, 2017).

Ekholm et al., "Combined Treatment With Saxagliptin Plus Dapagliflozin Reduces Insulin Levels by Increased Insulin Clearance and Improves β-Cell Function." *Endocrine Practice*, 23(3): 258-265 (Mar. 2017).

Forst et al., "Effects of sequentially adding empagliflozin and linagliptin on alpha and beta cell function in type 2 diabetic patients on previous metformin treatment—An exploratory mechanistic study." *Diabetes, Obesity and Metabolism*, 19(4):489-495 (2017).

Forst et al., "Clinical overview of linagliptin, a dipeptidyl peptidase-4 inhibitor, in patients with Type 2 diabetes mellitus." *Expert Review of Endocrinology and Metabolism*, 8(1): 21-35 (2013).

Friedrich et al., "A Randomized, Open-Label, Crossover Study to Evaluate the Pharmacokinetics of Empagliflozin and Linagliptin After Coadministration in Healthy Male Volunteers," *Clinical Theraputics*, 35(1): A33-A42 (Jan. 2013).

"GLYXAMBI® (empagliflozin and linagliptin) tablets, for oral use." 1-33 (Dec. 2016).

Guthrie, "Clinical use of dipeptidyl peptidase-4 and sodium-glucose cotransporter 2 inhibitors in combination therapy for type 2 diabetes mellitus", *Postgrad Med*, 127(5):463-479 (2015).

Hansen et al., "Postprandial dynamics of plasma glucose, insulin, and glucagon in patients with type 2 diabetes treated with saxagliptin plus dapagliflozin add-on to metformin therapy." *Endocrine Practice*, 20(11): 1187-1197 (Nov. 2014).

Harris, "The power of two: An update on fixed-dose combinations for type 2 diabetes." *Expert Review of Clinical Pharmacology*, 1-38 (Aug. 2016).

Hutchins et al., "A systematic review of adherence, treatment satisfaction and costs, in fixed-dose combination regimens in type 2 diabetes." *Current Medical Research and Opinion*, 27(6): 1157-1168 (2011).

Indian Patent Office, International Search Report in International Patent Application No. PCT/IN2022/050665, mailed Oct. 25, 2022, 3 pp.

Indian Patent Office, International Search Report in International Patent Application No. PCT/IN2022/050908, mailed Jan. 18, 2023, 3 pp.

Indian Patent Office, Written Opinion in International Patent Application No. PCT/IN2022/050665, mailed Oct. 25, 2022, 4 pp.

Indian Patent Office, Written Opinion in International Patent Application No. PCT/IN2022/050908, mailed Jan. 18, 2023, 6 pp.

Jabbour et al., "Dapagliflozin Is Effective as Add-on Therapy to Sitagliptin With or Without Metformin: A 24-Week, Multicenter, Randomized, Double-Blind, Placebo-Controlled Study." *Diabetes Care*, 37:740-750 (Mar. 2014).

Jain, "Empagliflozin/linagliptin single-pill combination therapy for patients with type 2 diabetes mellitus." *Expert Opinion on Pharmacotherapy*, 1-6 (2017).

Jay et al., "RP-HPLC Method Development and Validation for Estimation of Dapagliflozin Propanediol Monohydrate and Sitagliptin From Synthetic Mixture." *World Journal of Pharmacy and Pharmaceutical Sciences*, 10(7):1743-1757 (2021).

Jojima et al., "Empagliflozin (an SGLT2 inhibitor), alone or in combination with linagliptin (a DPP-4 inhibitor), prevents steatohepatitis in a novel mouse model of non-alcoholic steatohepatitis and diabetes." *Diabetology and Metabolic Syndrome*, 8(45): 1-11 (2016).

Kalra et al., "Fixed-dose combination in management of type 2 diabetes mellitus: Expert opinion from an international panel." *Journal of Family Medicine and Primary Care*, 9(11): 5450-5457 (Nov. 2020).

Kasahara et al., "Pharmacokinetic/Pharmacodynamic Drug-Drug Interaction Study of Tofogliflozin (a New SGLT2 Inhibitor) and Selected Anti-Type 2 Diabetes Mellitus Drugs." *Drug Research*, 1-8 (2015).

Kasichayanula et al., "Lack of pharmacokinetic interaction between dapagliflozin, a novel sodium-glucose transporter 2 inhibitor, and

(56) References Cited

OTHER PUBLICATIONS metformin, pioglitazone, glimepiride or sitagliptin in healthy subjects." *Diabetes, Obesity and Metabolism*, 13: 47-54 (2011).
Katsiki et al., "Fixed-dose combination of empagliflozin and linagliptin for the treatment of patients with type 2 diabetes mellitus: A systematic review and meta- analysis." *Diabetes, Obesity and Metabolism*, 22: 1001-1005 (2020).
Kaushal et al., "Clinical Safety and Recent Patents on Fixed-Dose Combinations of DPP-4 Inhibitors: an Updated Review." *Plant Archives*, 20(1): 3659-3666 (2020).
Kelleni, "Gliflozins: initial review of litera", *Integrative Obesity and Diabetes*, 2(5):276-276 (2016).
Kim et al., "Empagliflozin/Linagliptin: A Review in Type 2 Diabetes." *Drugs*, 75:1547-1557 (2015).
Lajara, "Use of the dipeptidyl peptidase-4 inhibitor linagliptin in combination therapy for type 2 diabetes," *Expert Opinion on Pharmacotherapy*, 13(18):2663-2671 (2012).
Lavalle-González et al., "Efficacy and safety of canagliflozin compared with placebo and sitagliptin in patients with type 2 diabetes on background metformin monotherapy: a randomised trial." *Diabetologia*, 56: 2582-2592 (2013).
Lewin et al., "Initial Combination of Empagliflozin and Linagliptin in Subjects With Type 2 Diabetes." *Diabetes Care*, 2-10 (Jan. 2015).
Mathieu et al., "A Randomized, Double-Blind, Phase 3 Trial of Triple Therapy With Dapagliflozin Add-on to Saxagliptin Plus Metformin in Type 2 Diabetes." *Diabetes Care*, 1-7 (2015).
Matthaei et al., "A Randomized, Double-Blind Trial of Triple Therapy With Saxagliptin Add-on to Dapagliflozin Plus Metformin in Patients With Type 2 Diabetes." *Diabetes Care*, 1-7 (Aug. 31, 2015).
Miller et al., "Ertugliflozin and Sitagliptin Co-initiation in Patients with Type 2 Diabetes: The Vertis Sita Randomized Study." *Diabetes Therapy*, 9: 253-268 (2018).
Musso et al., "A novel approach to control hyperglycemia in type 2 diabetes: Sodium glucose co-transport (SGLT) inhibitors. Systematic review and meta-analysis of randomized trials." *Annals of Medicine*, 44:4, 375-393 (2012).
Nizami et al., "Analytical method development and validation for simultaneous estimation of Ipragliflozin and Sitagliptin in tablet form by RP-HPLC method." *International Journal of Pharmacy and Life Sciences*, 9(7): 5860-5865 (Jul. 2018).
Oguma et al., "Changes in glucose-induced plasma active glucagon-like peptide-1 levels by co-administration of sodiumeglucose cotransporter inhibitors with dipeptidyl peptidase-4 inhibitors in rodents." *Journal of Pharacological Sciences*, 132(4): 255-261 (Dec. 2016).
Phani et al., "A Study of New Method Development, Validation and Forced Degradation for Simultaneous Analysis of Dapagliflozin and Saxagliptin in Pharmaceutical Dosage Form by HPLC Method." *Der Pharma Chemica*, 9(20): 96-103 (2017).
Pratley et al., "Ertugliflozin Plus Sitagliptin Versus Either Individual Agent Over 52 Weeks in Patients with Type 2 Diabetes Mellitus Inadequately Controlled With Metformin: The Vertis Factorial Randomized Trial." *Diabetes, Obesity and Metabolism*, 1-34 (2018).
"QTERN® (dapagliflozin and saxagliptin) tablets, for oral use." 1-42 (Feb. 2017).
Rizk et al., "Validated Voltammetric Method for the Simultaneous Determination of Anti-diabetic Drugs, Linagliptin and Empagliflozin in Bulk, Pharmaceutical Dosage Forms and Biological Fluids," *Electroanalysis*, 1-41 (2020).
Rizos et al., "Pharmacokinetic drug evaluation of empagliflozin plus linagliptin for the treatment of type 2 diabetes." *Expert Opinion on Drug Metabolism & Toxicology*, 1-34 (Dec. 15, 2017).
Roden et al., "Empagliflozin monotherapy with sitagliptin as an active comparator in patients with type 2 diabetes: a randomised, double-blind, placebo-controlled, phase 3 trial." *Lancet Diabetes Endocrinal*, 1:208-2019 (Nov. 2013).
Rosenstock et al., "Dual Add-on Therapy in Type 2 Diabetes Poorly Controlled With Metformin Monotherapy: A Randomized Double-Blind Trial of Saxagliptin Plus Dapagliflozin Addition Versus Single Addition of Saxagliptin or Dapaglif lozin to Metformin." *Diabetes Care*, 1-8 (Oct. 2014).
Satoh-Asahara et al., "A dipeptidyl peptidase-4 inhibitor, sitagliptin, exerts anti-inflammatory effects in type 2 diabetic patients" *Metabolism Clinical and Experimental*, 62: 347-351 (Mar. 2013).
Scheen, "Drug-Drug Interactions with Sodium-Glucose Cotransporters Type 2 (SGLT2) Inhibitors, New Oral Glucose-Lowering Agents for the Management of Type 2 Diabetes Mellitus." *Clinical Pharmacokinetics*, 1-10 (Jan. 2014).
Scheen, "Pharmacokinetic Characteristics and Clinical Efficacy of an SGLT2 Inhibitor Plus DPP-4 Inhibitor Combination Therapy in Type 2 Diabetes." *Clinical Pharmacokinetics*, 1-16 (Dec. 30, 2016).
Scheen, "SGLT2 Inhibitors: Benefit/Risk Balance," *Current Diabetes Reports*, 16(92): 1-11 (Aug. 19, 2016).
Scheen, "Evaluating SGLT2 inhibitors for type 2 diabetes: pharmacokinetic and toxicological considerations." *Expert Opinion on Drug Metabolism and Toxicology*, 10(5):647-663 (2014).
Scheen, "DPP-4 inhibitor plus SGLT-2 inhibitor as combination therapy for type 2 diabetes: from rationale to clinical aspects", *Expert Opinion on Drug Metabolism and Toxicology* , 1-37 (2016).
Scheen, "A review of gliptins in 2011." *Expert Opinion Pharmacotherapy*, 13(1): 81-99 (2012).
Scheen, "Dapagliflozin and Saxagliptin Tablets for Adults with Type 2 Diabetes." *Expert Review of Clinical Pharmacology*, 1-44 (Oct. 2017).
Scheen et al., "Gliptin-gliflozin combination in the treatment of type 2 diabetes", *Reef Med Suisse*, 12:1384-8 (2016).
Sharma, "Potential for combination of dipeptidyl peptidase-4 inhibitors and sodium-glucose co-transporter-2 inhibitors for the treatment of type 2 diabetes", *Diabetes, Obesity and Metabolism*, 17:616-621 (2015).
Sheikh et al., "Development and Validation of Rapid Stability-Indicating High-Performance Liquid Chromatography Method for the Determination of Linagliptin and Empagliflozin in Pure and Dosage Forms." *Asian Journal of Pharmaceutical and Clinical Research*, 13(4): 172-177 (2020).
Singh et al., "Sodium-glucose co-transporter-2 inhibitors and dipeptidyl peptidase-4 inhibitors combination therapy in type 2 diabetes: A systematic review of current evidence," *Indian Journal of Endocrinology and Metabolism*, 20(2): 245-253 (Mar. 2016).
Smulders et al., "No pharmacokinetic interaction between ipragliflozin and sitagliptin, pioglitazone, or glimepiride in healthy subjects." *Diabetes, Obesity and Metabolism*, 1-7 (2012).
Søfteland et al., "Empagliflozin as Add-on Therapy in Patients With Type 2 Diabetes Inadequately Controlled With Linagliptin and Metformin: A 24-Week Randomized, Double-Blind, Parallel-Group Trial." *Diabetes Care*, 1-9 (Dec. 2016).
Tahara et al., "Effects of the combination of SGLT2 selective inhibitor ipragliflozin and various antidiabetic drugs in type 2 diabetic mice." *Archives of Pharmacal Research*, 1-12 (2015).
Tan et al., "Empagliflozin/Linagliptin: Combination therapy in patients with type 2 diabetes." *Annales d'Endocrinologie*, 1-6 (2016).
Terauchi et al., "Long-term safety and efficacy of the sodium-glucose cotransporter 2 inhibitor, tofogliflozin, added on glucagon-like peptide-1 receptor agonist in Japanese patients with type 2 diabetes mellitus: A 52-week open-label, multicenter, post-marketing clinical study." *Journal of Diabetes Investigation*, 10(6): 1518-1526 (Nov. 2019).
Tinahones et al., "Linagliptin as add-on to empagliflozin and metformin in patients with type 2 diabetes: two 24-week randomized, double-blind, double-dummy, parallel-group trials." *Diabetes, Obesity and Metabolism*, 1-35 (2016).
Triplitt et al., "Empagliflozin and linagliptin combination therapy for treatment of patients with type 2 diabetes mellitus." *Expert Opinion on Pharmacotherapy*, 1-15 (Nov. 2015).
Vakkalagadda et al., "Lack of a Pharmacokinetic Interaction Between Saxagliptin and Dapagliflozin in Healthy Subjects: A Randomized Crossover Study." *Clinical Theraputics*, 1-10 (2016).
Vakkalagadda et al., "Bioequivalence of saxagliptin/dapagliflozin fixed-dose combination tablets compared with coadministration of

(56) References Cited

OTHER PUBLICATIONS the individual tablets to healthy subjects." *Pharmacology Research and Perspectives*, 3(6): 1-12 (Nov. 19, 2015).
Vaseem et al., "SGLT2 Inhibitor and DPP4 Inhibitor Co-Administration in Type 2 Diabetes—Are We Near The 'Promised Land'?", *Research & Reviews: Journal of Pharmacology and Toxicological Studies*, 4(1):6-11 (2016).
Williams et al., "Combination therapy with saxagliptin and dapagliflozin for the treatment of type 2 diabetes." *Expert Opinion on Pharmacotherapy*, 16(15): 2373-2379 (2015).
Woo, "Empagliflozin/linagliptin single-tablet combination: first-in-class treatment option." *International Journal of Clinical Practice*, 69(12): 1427-1437 (Dec. 2015).
Zinman, "Initial Combination Therapy for Type 2 Diabetes Mellitus: Is It Ready for Prime Time?." *American Journal of Medicine*, 124(1S): S19-S34 (Jan. 2011).

* cited by examiner

PHARMACEUTICAL COMPOSITION COMPRISING COMBINATION OF SITAGLIPTIN AND EMPAGLIFLOZIN

PRIORITY APPLICATION

This application is the U.S. national phase of International Application No. PCT/IN2022/050908, filed on Oct. 10, 2022, which claims the benefit of priority of our Indian Patent Application number 202121046486 filed on Oct. 12, 2021 which is incorporated herein by reference and disclosures of which is incorporated in the instant application.

FIELD OF INVENTION

The present invention relates to a stable pharmaceutical composition comprising combination of a therapeutically effective amount of Dipeptidyl peptidase-4 (DPP4) inhibitor and a therapeutically effective amount of Sodium-glucose co-transporter-2 (SGLT2) inhibitor for reducing blood glucose level in patients with diabetes. The present invention specifically relates to a stable pharmaceutical composition comprising Sitagliptin or a pharmaceutically acceptable salts or solvates or hydrates or premix thereof and Empagliflozin or a pharmaceutically acceptable salts or solvates or hydrates or premix thereof in the presence of one or more pharmaceutically acceptable excipients. Further, the invention relates to a stable pharmaceutical composition comprising Sitagliptin and Empagliflozin present in a ratio in the range from about 20:1 to about 1:1. Moreover, the present invention relates to a stable pharmaceutical composition comprising Sitagliptin Phosphate Monohydrate, Empagliflozin and one or more pharmaceutically acceptable excipients with high content uniformity, reduced degradation impurities and optimum dissolution.

BACKGROUND OF THE INVENTION

Type 2 diabetes is a chronic and progressive disease arising from a complex pathophysiology involving the dual endocrine defects of insulin resistance and impaired insulin secretion. The treatment of Type 2 diabetes typically begins with diet and exercise, followed by oral antidiabetic monotherapy.

For many patients, individual drug regimens do not sufficiently control glycaemia during long-term treatment, leading to a requirement for combination therapy within several years following diagnosis. However, co-prescription of two or more oral antidiabetic drugs may result in treatment regimens that are complex and difficult for many patients to follow. Combining two or more oral antidiabetic agents into a single tablet provides a potential means of delivering combination therapy without adding to the complexity of patients' daily regimens.

Selection of effective and well-tolerated treatments is a key step in the design of a combination tablet. Two novel classes of glucose-lowering agents that meet these criteria are the dipeptidyl peptidase-4 (DPP-4) inhibitors and the sodium glucose cotransporter-2 (SGLT2) inhibitors. The complementary modes of action of SGLT-2 inhibitors and DPP-4 inhibitors suggest that they have the potential to be combined in form of a fixed dose combination in a clinical setting.

Sitagliptin is a novel Dipeptidyl peptidase-4 (DPP-IV) inhibitor represented by following chemical structure:

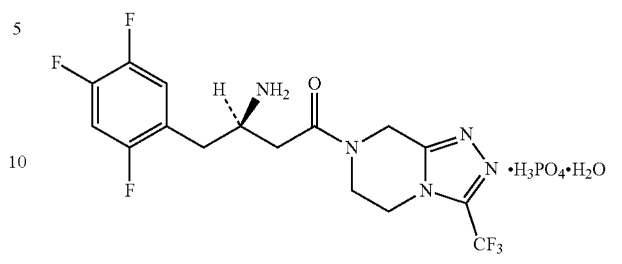

Chemical Structure of Sitagliptin Phosphate Monohydrate

The chemical name for Sitagliptin is 7-[(3R)-3-amino-1-oxo-4-(2,4,5-trifluorophenyl)butyl]-5,6,7,8-tetrahydro-3-(trifluoromethyl)-1,2,4-triazolo[4,3-a]pyrazine phosphate (1:1) monohydrate. Sitagliptin is a white to off-powder and exhibits pH dependent aqueous solubility. It is soluble in water and N,N-dimethyl formamide, slightly soluble in methanol, soluble in ethanol, acetone and acetonotrile and insoluble in isopropanol and isopropyl acetate.

It was developed by Merck & Co. Ltd and is approved as Januvia® in the United States of America and in Europe. Sitagliptin is approved as 25 mg, 50 mg and 100 mg immediate release tablet dosage form for once daily administration for adult patients with type 2 diabetes mellitus, Januvia® is indicated to improve glycaemic control as monotherapy, as dual therapy in combination with Metformin, a sulphonyl urea, or a thiazolidinedione and as a triple therapy in combination with a sulphonyl urea and metformin or a thiazolidinedione and metformin. Januvia® is also indicated as add-on to insulin (with or without metformin).

U.S. Pat. No. 6,699,871 discloses Sitagliptin and pharmaceutically acceptable salts thereof and individual diastereomers thereof. It also discloses its pharmaceutical composition comprising Sitagliptin and an inert carrier, its use in the treatment of diabetes and its method of preparation.

U.S. Pat. No. 7,326,708 discloses a dihydrogenphosphate salt of Sitagliptin or a hydrate thereof, a crystalline monohydrate with specific XRD, NMR, Mass characteristics, its pharmaceutical composition, process for preparation and method of treatment of type 2 diabetes using the same.

Empagliflozin is a novel orally administered, potent, and selective SGLT 2 inhibitor represented by following chemical structure:

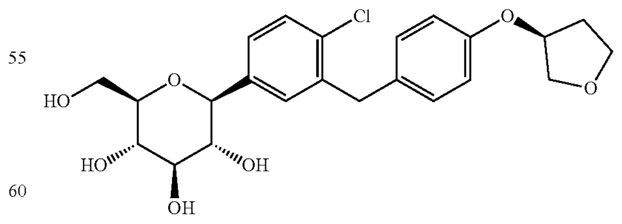

Chemical Structure of Empagliflozin

The chemical name for Empagliflozin is (1S)-1,5-anhydro-1-(4-chloro-3-{4-[(3S)-tetrahydrofuran-3-yloxy]

benzyl}phenyl)-D-glucitol, also known as D-Glucitol,1,5-anhydro-1-C-[4-chloro-3-[[4-[[(3S)-tetrahydro-3-furanyl]oxy]phenyl]methyl]phenyl]-(1S). Empagliflozin is a white to yellowish non-hygroscopic crystalline solid, very slightly soluble in water (pH 1-7.4), slightly soluble in acetonitrile and ethanol, sparingly soluble in methanol, and practically insoluble in toluene. A single polymorphic form has been observed for Empagliflozin which is non-solvated and non-hydrated.

It was developed by Boehringer Ingelheim International GmbH and is approved under brand name Jardiance® in Europe and United States of America. Empagliflozin is approved as 10 mg and 25 mg immediate release tablet dosage form for once daily administration for the treatment of adults with insufficiently controlled type 2 diabetes mellitus as an adjunct to diet and exercise as monotherapy when metformin is considered inappropriate due to intolerance and in addition to other medicinal products for the treatment of diabetes. Jardiance® is also indicated in adults for the treatment of symptomatic chronic heart failure with reduced ejection fraction.

U.S. Pat. No. 7,579,449 discloses Empagliflozin, the stereoisomers thereof, the mixtures thereof and the salts thereof. It also discloses its method of preparation, its use in the treatment of metabolic disorders including diabetes mellitus as well as its pharmaceutical composition along with specific excipients.

U.S. Pat. No. 7,713,938 discloses crystalline form of Empagliflozin that comprises characteristic 2θ peaks, along with its method of preparation, its pharmaceutical composition and its use in the treatment of metabolic disorders including diabetes mellitus.

WO2010/092126 discloses specific pharmaceutical composition comprising Empagliflozin having a specific particle size distribution of 1 μm<=X90<200 μm in the said composition and wherein Empagliflozin represents 25% or less of the weight of said composition.

Tobias Brand (Adv Ther (2012) 29(10):889-899.) et. al., have supported coadministration of Empagliflozin and Sitagliptin without specifying any clinically relevant effect on the ph'cokinetics of either drug in healthy volunteers.

André J. Scheen et al. (Clin Pharmacokinet, Springer International Publishing Switzerland 2016) studied and concluded the combination as an attractive therapeutic strategy because the complementary modes of action of the two medications Empagliflozin and Sitagliptin contribute to improve blood glucose control in patients with T2D, without deteriorating the safety/tolerance profile of each compound.

WO2020/130502 merely discloses specific monolayer pharmaceutical composition comprising Empagliflozin and Sitagliptin as active ingredients along with specific excipients.

Although the above prior arts disclose concomitant product administration of Sitagliptin and Empagliflozin for the patients suffering from diabetes mellitus, none of the prior arts disclose a pharmaceutical product containing a fixed dose combination of Sitagliptin phosphate monohydrate and Empagliflozin and potential generation of impurities due to any possible interaction of Empagliflozin or Sitagliptin with customary excipients or when Sitagliptin and Empagliflozin of different crystalline or amorphous form are combined together in a single formulation and hence there is an unmet clinical need to develop the same.

In an attempt to prepare pharmaceutical compositions of selected DPP-4 inhibitors it has been observed, that the DPP-4 inhibitors with a primary or secondary amino group show incompatibilities, degradation problems, or extraction problems with a number of customary excipients such as microcrystalline cellulose, sodium starch glycolate, croscarmellose sodium, tartaric acid, citric acid, glucose, fructose, saccharose, lactose, maltodextrines. Though the compounds themselves are very stable, they react with incompatible partner drug, or its impurity product, and/or with many excipients used in solid dosage forms and with impurities of excipients, especially in tight contact provided in tablets and at high excipient/drug ratios. The amino group appears to react with reducing sugars and with other reactive carbonyl groups and with carboxylic acid functional groups formed for example at the surface of microcrystalline cellulose by oxidation. Thus, pharmaceutical compositions are required to solve these technical problems, which may be associated with the selected DPP-4 inhibitor compounds.

The European assessment report of Jardiance® discloses that Empagliflozin is BCS class III molecule and is slightly soluble in aqueous media between pH 1-7.4 and has low intestinal permeability. Particle size is not found to be critical for dissolution, but since coarser API dissolves slightly more slowly, the drug substance is milled and particle size is tightly controlled. Prakash Niguram et. al., (DOI: 0.1080/03639045.2020.1716371) has reported interaction of Empagliflozin with macrogol which is used in coating of many pharmaceutical compositions and is also present in Jardiance®. SGLT2 inhibitors are also known to be incompatible with dibasic calcium phosphate.

Sitagliptin phosphate monohydrate is crystalline in nature with good flow properties, compressibility and is used in non-micronized form. Whereas Empagliflozin needs to be milled and its particle size needs to be tightly controlled.

Sitagliptin and Empagliflozin differs in terms of the solubility, particle size distribution, stability, and compressibility and flow properties and the development of a pharmaceutical composition comprising a fixed dose combination of Sitagliptin and Empagliflozin is very challenging due to markedly different physico-chemical properties, different solubility profile as well as different compatibility profile of each API.

The inventors of the present invention have overcome the problems associated with the currently marketed individual products and have developed a stable pharmaceutical composition comprising a fixed dose combination of Sitagliptin or a pharmaceutically acceptable salt or solvate or hydrate or premix thereof and Empagliflozin or a pharmaceutically acceptable salt or solvate or hydrate or premix thereof in single product with reduced amount of impurities, high content uniformity and optimum dissolution.

The fixed dose combination product of Sitagliptin and Empagliflozin would facilitate long unmet need of a simplified dosage regimen wherein the patients can be treated with only a single product. This will also lead to an increase in patient compliance and adherence considering long period of treatment associated with chronic disease and will reduce the pill burden.

SUMMARY OF THE INVENTION

The present invention relates to a pharmaceutical composition comprising a fixed dose combination of DPP-IV inhibitor and SGLT2 inhibitor and one or more pharmaceutically acceptable excipients for the treatment of diabetes mellitus.

The present invention specifically relates to a stable pharmaceutical composition comprising Sitagliptin or a pharmaceutically acceptable salt or solvate or hydrate or premix thereof, Empagliflozin or a pharmaceutically acceptable salt or solvate or hydrate or premix thereof and one or more pharmaceutically acceptable excipients for the treatment of diabetes mellitus.

In another aspect of the invention, there is provided a pharmaceutical composition comprising a fixed dose combination of about 25 mg to 100 mg Sitagliptin or equivalent amount of its salt or solvate or hydrate or premix thereof and about 5 mg to 25 mg of Empagliflozin or equivalent amount of its salt or solvate or hydrate or premix thereof wherein Sitagliptin and Empagliflozin are present in a ratio in the range from about 20:1 to about 1:1.

The present invention specifically relates to a stable pharmaceutical composition comprising Sitagliptin or a pharmaceutically acceptable salt or solvate or hydrate or premix thereof, Empagliflozin or a pharmaceutically acceptable salt or solvate or hydrate or premix thereof, and pharmaceutically acceptable excipient which exhibits optimum content uniformity despite the difference in the physical properties & differing dose of individual API.

The present invention specifically relates to a stable pharmaceutical composition comprising Sitagliptin or a pharmaceutically acceptable salt or solvate or hydrate or premix thereof, Empagliflozin or a pharmaceutically acceptable salt or solvate or hydrate or premix thereof, and pharmaceutically acceptable excipient which is bioequivalent to individual product of Sitagliptin and Empagliflozin.

The present invention further relates to pharmaceutical composition for oral administration for treatment of diabetes mellitus comprising Sitagliptin or a pharmaceutically acceptable salt or solvate or hydrate or premix thereof, Empagliflozin or a pharmaceutically acceptable salt or solvate or hydrate or premix thereof, and pharmaceutically acceptable excipient wherein the composition remains stable at 40° C.±2° C./75% RH±5% RH conditions for a time period of at least 6 months.

Moreover, the present invention relates to pharmaceutical composition comprising Sitagliptin or a pharmaceutically acceptable salt or solvate or hydrate or premix thereof, Empagliflozin or a pharmaceutically acceptable salt or solvate or hydrate or premix thereof and optionally a stabilizer, wherein the composition retains at least 90% of amount of Sitagliptin and Empagliflozin initially present in the composition.

The present invention also relates to a pharmaceutical composition comprising a fixed dose combination of Sitagliptin or a pharmaceutically acceptable salt or solvate or hydrate or premix thereof with Empagliflozin or a pharmaceutically acceptable salt or solvate or hydrate or premix thereof and optionally a stabilizer, wherein any of the known and unknown impurity for Sitagliptin is not more than 0.2%, the total impurity for Sitagliptin is not more than 2%, whereas for Empagliflozin, any of the known impurity is not more than 0.5%, any of the unknown impurity is not more than 0.2% and the total impurity is not more than 2%.

The present invention also relates to a pharmaceutical composition comprising a fixed dose combination of Sitagliptin or a pharmaceutically acceptable salt or solvate or hydrate or premix thereof, Empagliflozin or a pharmaceutically acceptable salt or solvate or hydrate or premix thereof wherein the dosage form releases more than 75% of both Sitagliptin and Empagliflozin within 30 minutes.

DETAILED DESCRIPTION

The present invention relates to a stable pharmaceutical composition comprising fixed dose combination of a therapeutically effective amount of DPP-IV inhibitor and a therapeutically effective amount of SGLT-2 inhibitor for the prevention, treatment or prophylaxis of diabetes.

Specifically, the present invention relates to a stable pharmaceutical composition comprising a therapeutically effective amount of Sitagliptin or a pharmaceutically acceptable salt or solvate or hydrate or premix thereof and a therapeutically effective amount of Empagliflozin or a pharmaceutically acceptable salt or solvate or hydrate or premix thereof and one or more pharmaceutically acceptable excipients for the prevention, treatment or prophylaxis of diabetes.

As used herein, the term "Sitagliptin" refers to compound which may be present in its base form or any of its pharmaceutically acceptable salt or polymorph or solvate or hydrate or premix or prodrug or metabolite or analog or isomer or like thereof.

As used herein, the term "Empagliflozin" refers to compound which may be present in base form or in the form of the pharmaceutically acceptable salt or polymorph or solvate or hydrate or premix or prodrug or metabolite or analog or isomer or like thereof.

As used herein, the term "pharmaceutically acceptable salts" include, but are not limited to mineral or organic salts of basic residues such as amines, alkali or mineral or organic salts of acidic residues such as carboxylic acids and the like thereof.

Further, the pharmaceutically acceptable salts include the conventional non-toxic salts or the quaternary ammonium salts. The conventional non-toxic salts include inorganic or organic acids, for example those derived from inorganic acids such as hydrochloric, phosphoric and the like thereof; and the salts prepared from organic acids such as acetic, succinic, malic, tartaric, citric, benzoic, salicyclic, fumaric, toluenesulfonic, methanesulfonic, oxalic, and the like thereof.

As used herein, the term "therapeutically effective amount of Sitagliptin" is an amount of Sitagliptin or its pharmaceutically acceptable salt which eliminates, alleviates, or provides relief in diabetes mellitus.

As used herein, the term "therapeutically effective amount of Empagliflozin" is an amount of Empagliflozin or its pharmaceutically acceptable salt which eliminates, alleviates, or provides relief in diabetes mellitus.

The term "stable" means a drug substance and/or pharmaceutical composition for pharmaceutical use which remains stable as per ICH guidelines. The term "ICH guidelines" means drug substance and composition remains stable for longer period of time at 25° C.±2° C./60% RH±5% RH, 30° C.±2° C./65% RH±5% RH, and 40° C.±2° C./75% RH±5% RH conditions for a period of at least 6 months.

As used herein, the terms "about" and "approximately" should be understood to mean within an acceptable range for the particular value as determined by one of ordinary skill in the art, which will depend in part on how the value is measured or determined, i.e., the limitations of the measurement system. For example, "about" can mean a range of up to 30%, preferably up to 20%, preferably up to 10%, more preferably up to 5%, and more preferably still up to 1% of a given value.

As used herein, the terms "bioequivalence" is defined as a pharmacokinetic (PK) comparison of the present pharmaceutical composition to that of the approved formulation. The pharmaceutical composition of the present invention must display drug pharmacokinetics that fall within a range of 80-125% (0.8-1.25) when one computes the ratio of the drug PK of the present invention composition with respect to approved marketed formulation.

As used herein, the term "impurity" include total impurities or individual, known or unknown impurities.

According to one aspect of the invention, there is provided a stable pharmaceutical composition comprising from about 25 mg to about 100 mg of Sitagliptin or a pharmaceutically acceptable salt or solvate or hydrate or premix thereof.

According to one another aspect of the invention, there is provided a stable pharmaceutical composition comprising about from about 5 mg to 25 mg of Empagliflozin or a pharmaceutically acceptable salt or solvate or hydrate or premix thereof.

According to one another aspect, there is provided a stable pharmaceutical composition comprising Sitagliptin and Empagliflozin wherein Sitagliptin and Empagliflozin are present in a ratio in the range from about 20:1, preferably in the range of from about 10:1, to about 1:1. In a preferred embodiment, the pharmaceutical composition comprises Sitagliptin and Empagliflozin are present in a ratio of about 4:1.

According to yet one another aspect, there is provided a stable pharmaceutical composition comprising Sitagliptin and Empagliflozin wherein Sitagliptin and Empagliflozin are present in a dose of 25/5 mg, 25/10 mg 25/12.5 mg, 25/25 mg, 50/5 mg, 50/10 mg, 50/12.5 mg, 50/25 mg, 100/5 mg, 100/10 mg, 100/12.5 mg, 100/25 mg respectively.

In one embodiment of the aspect, the present invention relates to a stable pharmaceutical composition comprising Sitagliptin or a pharmaceutically acceptable salt or solvate or hydrate or premix thereof, Empagliflozin or a pharmaceutically acceptable salt or solvate or hydrate or premix thereof and one or more pharmaceutically acceptable excipients in form of a single layer or a bilayer tablet.

In one aspect of the embodiment, the present invention relates to a stable pharmaceutical composition comprising a first portion and a second portion, wherein the first portion comprises Sitagliptin or pharmaceutically acceptable salt or solvate thereof in form of powder or granules along with one or more pharmaceutically acceptable excipient; the second portion comprises Empagliflozin or pharmaceutically acceptable salt or solvate thereof in form of powder or granules along with one or more pharmaceutically acceptable excipients.

In one another aspect, the present invention relates to a stable pharmaceutical composition comprising Sitagliptin or a pharmaceutically acceptable salt or solvate or hydrate or premix thereof, Empagliflozin or a pharmaceutically acceptable salt or solvate or hydrate or premix thereof along with one or more pharmaceutically acceptable excipients, wherein Sitagliptin is in form of granules and Empagliflozin is also in form of separate granules.

In one another aspect, the present invention relates to a stable pharmaceutical composition comprising Sitagliptin or a pharmaceutically acceptable salt or solvate or hydrate or premix thereof, Empagliflozin or a pharmaceutically acceptable salt or solvate or hydrate or premix thereof along with one or more pharmaceutically acceptable excipients and optionally a stabilizer, wherein Sitagliptin is in form of granules and Empagliflozin is added extra-granularly in form of powder or vice versa Empagliflozin is present intra-granularly and Sitagliptin is added extra-granularly.

In one another aspect, the present invention relates to a stable bilayer pharmaceutical composition comprising Sitagliptin or a pharmaceutically acceptable salt or solvate or hydrate or premix thereof, Empagliflozin or a pharmaceutically acceptable salt or solvate or hydrate or premix thereof along with one or more pharmaceutically acceptable excipients, wherein Sitagliptin and Empagliflozin are present in separate layers.

In one aspect, the present invention relates to a stable pharmaceutical composition comprising Sitagliptin or a pharmaceutically acceptable salt or solvate or hydrate or premix thereof, Empagliflozin or a pharmaceutically acceptable salt or solvate or hydrate or premix thereof and pharmaceutically acceptable stabilizers.

In another embodiment of the aspect, the pharmaceutical composition of the present invention comprises one or more stabilizer along with Sitagliptin part or with the Empagliflozin part of the composition to limit the generation of impurity. Alternatively the stabilizer may also be present in both the parts.

In another embodiment, the pharmaceutical composition comprising Sitagliptin, Empagliflozin and one or more pharmaceutically acceptable excipient wherein the composition remains stable at 25° C.±2° C./60% RH±5% RH, 30° C.±2° C./65% RH±5% RH, and 40° C.±2° C./75% RH±5% RH conditions for a time period of at least 6 months and wherein the composition retains at least 90% of amount of Sitagliptin and Empagliflozin initially present in the composition In another embodiment, the pharmaceutical composition comprising Sitagliptin, Empagliflozin and one or more pharmaceutically acceptable excipient wherein the composition remains stable at 25° C.±2° C./60% RH±5% RH, 30° C.±2° C./65% RH±5% RH, and 40° C.±2° C./75% RH±5% RH conditions for a time period of at least 6 months and wherein any of the known and unknown impurity for Sitagliptin is not more than 0.2%, the total impurity for Sitagliptin is not more than 2%, whereas for Empagliflozin, any of the known impurity is not more than 0.5%, any of the unknown impurity is not more than 0.2% and the total impurity is not more than 2%.

The present invention also relates to a pharmaceutical composition comprising a fixed dose combination of Sitagliptin and Empagliflozin wherein the dosage form releases more than 75% of both Sitagliptin and Empagliflozin within 30 minutes.

The active pharmaceutical ingredient Sitagliptin and Empagliflozin in the present invention composition may be present in any one or more polymorphic form selected from crystalline, amorphous, a solvate, a hydrate, a premix or an anhydrous or a like thereof.

In another embodiment, the pharmaceutical compositions comprising Sitagliptin having a particle size $D_{90}$ less than about 200 μm, preferably less than about 150 μm, more preferably less than about 100 μm.

In one embodiment, the pharmaceutical compositions comprising Empagliflozin having a particle size $D_{90}$ from about 1 to about 200 μm, preferably from about 1 to about 150 μm, more preferably from about 1 to 100 μm, even more preferably from about 1 to 50 μm.

In one embodiment, the pharmaceutical composition comprises from about 1% to about 90% w/w Sitagliptin, preferably from about 3% to about 80% w/w Sitagliptin, more preferably from about 5% to about 70% w/w Sitagliptin of the total weight of the composition and one or more pharmaceutically acceptable excipients.

In another embodiment, the pharmaceutical composition comprises from about 0.1% to about 30% w/w Empagliflozin, preferably from about 0.5% to about 15% w/w Empagliflozin, more preferably from about 1 to about 10% w/w Empagliflozin of the total weight of the composition and one or more pharmaceutically acceptable excipients.

The present invention specifically relates to a stable pharmaceutical composition comprising Sitagliptin or a pharmaceutically acceptable salt or solvate or hydrate or premix thereof, Empagliflozin or a pharmaceutically acceptable salt or solvate or hydrate or premix thereof, and pharmaceutically acceptable excipient which shows optimum content uniformity.

The present invention specifically relates to a stable pharmaceutical composition comprising Sitagliptin or a pharmaceutically acceptable salt or solvate or hydrate or premix thereof, Empagliflozin or a pharmaceutically acceptable salt or solvate or hydrate or premix thereof, and one or more pharmaceutically acceptable excipient which is bioequivalent to individual marketed drug products.

According to another aspect, the present invention is directed to a solid pharmaceutical composition for oral administration which comprises Sitagliptin or a pharmaceutically acceptable salt or solvate or hydrate or premix thereof and Empagliflozin or a pharmaceutically acceptable salt or solvate or hydrate or premix thereof, with one or more excipients, in a pharmacokinetically effective ratio such that said Sitagliptin and said Empagliflozin are released in a therapeutically effective, non-toxic amount and in bioequivalent manner.

In still another embodiment, the formulation may be a tablet in which either one or both of Sitagliptin or Empagliflozin are dissolved/dispersed along with the binder solution optionally along with one or more stabilizer.

The present invention further relates to a process of preparing pharmaceutical composition comprising a fixed dose formulation of Sitagliptin or a pharmaceutically acceptable salt or solvate or hydrate or premix thereof and Empagliflozin or a pharmaceutically acceptable salt or solvate or hydrate or premix thereof by direct compression or by dry granulation or by wet granulation or by any other method known to the person skilled in the art.

In one embodiment, the present invention relates to pharmaceutical composition comprising Sitagliptin or a pharmaceutically acceptable salt or solvate or hydrate or premix thereof, Empagliflozin or a pharmaceutically acceptable salt or solvate or hydrate or premix thereof and one or more pharmaceutically acceptable excipients which is free of excipients with which either Empagliflozin or Sitagliptin may be incompatible.

In another embodiment, the pharmaceutical composition of the invention may include one or more pharmaceutically acceptable excipients selected from diluent, binder, disintegrant/super-disintegrant, lubricant, glidant, colouring agent, flavouring agent, sweetening agent, stabilizer, solvent, suitable film-forming agents or a like thereof.

The diluents according to the present invention include, but are not limited to, starch (maize starch, potato starch, rice starch, wheat starch, pregelatinized starch, partially Pregelatinized starch and others), lactose (e.g., lactose monohydrate, such as Fast Flo® 316, lactose anhydrous and others), cellulose derivatives includes crystalline celluloses such as microcrystalline cellulose (MCC), kaolin and powdered celluloses, confectioner's sugar, calcium carbonate, magnesium carbonate, dibasic calcium phosphate, tribasic calcium phosphate, dicalcium phosphate, calcium sulfate, carmellose, sugar alcohols such as mannitol, sorbitol, xylitol, inositol sucrose, inositol, polysaccharides polymers such as pullulan and mixtures thereof. Preferably, the diluent in present invention is Pregelatinized starch, microcrystalline cellulose, lactose and dibasic calcium phosphate. The diluent may be present in an amount from about 5% to about 90% w/w of the composition, preferably from about 10% to about 80% w/w of the composition and more preferably from about 20% to about 70% w/w of the composition.

The binders according to the present invention include, but are not limited to, corn starch, potato starch, or other starches, gelatin, natural and synthetic gums such as acacia, sodium alginate, alginic acid, other alginates, powdered tragacanth, guar gum, cellulose and its derivatives (e.g., ethyl cellulose, cellulose acetate, carboxymethyl cellulose calcium, sodium carboxymethyl cellulose), polyvinyl pyrrolidone (PVP) and its derivatives in various grades such as povidone, copovidone and others, methyl cellulose, pregelatinized starch, hydroxypropyl cellulose (HPC/Hyprolose), hydroxypropyl methyl cellulose (HPMC/Hypromellose) in various grades, microcrystalline cellulose and mixtures thereof. The binder may present in an amount from about 0% to about 20% w/w of the composition, preferably from about 0.1% to about 10% w/w of the composition and more preferably from about 0.5% to about 5% of the composition.

The disintegrants/super-disintegrants according to the present invention include, but are not limited to, low-substituted hydroxypropyl cellulose (L-HPC), microcrystalline cellulose (MCC), sodium starch glycolate (SSG), alginic acid, calcium carbonate, croscarmellose sodium (CCS), crospovidone, polacrillin potassium, maize, potato or tapioca starch, pre-gelatinized starch, partially pregelatinized starch and mixtures thereof. The disintegrant present either alone or in combination with other disintegrants and the preferred disintegrant is croscarmellose sodium and low-substituted hydroxypropyl cellulose. The disintegrant may present in amount from about 0.1% to about 20% w/w of the composition, preferably from about 0.5% to about 10% w/w of the composition and more preferably about 1 to 5% w/w of the composition.

The lubricants according to the present invention include, but are not limited to, magnesium stearate, glyceryl monostearates, glyceryl behenate, palmitic acid, talc, carnauba wax, calcium stearate, zinc stearate, polyoxyethylene monostearates, calcium silicate, silicon dioxide, hydrogenated vegetable oils and fats, stearic acid, sodium stearyl fumarate (SSF), sodium lauryl sulphate and mixtures thereof.

Preferably, the lubricant in present invention is magnesium stearate &/or sodium stearyl fumerate. The lubricants may present in an amount from about 0.05 to about 5% w/w of the composition, preferably from about 0.1% to about 3% w/w of the composition.

The glidants according to the present invention include, but are not limited to, silica such as colloidal silicon dioxide or kaolin, talc and mixtures thereof. Preferably, the glidant in present invention is colloidal silicone dioxide. The glidants may present in amount from about 0.01% to about 5% w/w of the composition, preferably from about 0.1% w/w to about 2% w/w of the composition.

The colouring agents according to the present invention include, but are not limited to, natural colorants, synthetic colorants or like thereof. Examples of natural colorants include pigments and dyes obtained from mineral, plant, and animal sources like red ferric oxide, titanium dioxide, yellow ferric oxide, zinc oxide, indigo and synthetic colorants include FD&C or D&C dye, an azo dye or a like thereof. The colouring agents may be present in the composition as per the quantity sufficient requirement, preferably from about 0.1% to about 2.0 w/w of the composition.

The stabilizers may be included in the compositions of the present invention depending upon the requirement which include, but are not limited to acidic compound selected from the group comprising acetic acid, glacial acetic acid, citric acid, fumaric acid, hydrochloric acid, malic acid, nitric acid, phosphoric acid, propionic acid, sulfuric acid, tartaric acid, benzoic acid, sodium benzoate and the like or basic compound selected from the group comprising basic amino acids such as L-arginine, L-lysine, L-histidine, L-citrulline, cysteine, 6-amino caproic acid and the like or basic/alkalizing agents selected from the group comprising ammonium carbonate, sodium carbonate, monoethanolamine, diethanolamine, potassium hydroxide, sodium hydroxide, potassium carbonate and the like or buffering agents selected from the group comprising acetic acid, adipic acid, ammonium carbonate, ammonium phosphate, boric acid, citric acid, lactic acid, phosphoric acid, potassium citrate, potassium metaphosphate, potassium phosphate monobasic, potassium phosphate dibasic, sodium acetate, sodium citrate, sodium lactate, sodium phosphate monobasic, sodium phosphate dibasic, succinic acid and the likes. The stabilizer may further include antioxidant substances which is present in amounts effective to retard decomposition of a drug that is susceptible to oxidation.

The antioxidants according to the present application include, but are not limited to include one or more of ascorbic acid and its salts, tocopherols, sulfite salts such as sodium metabisulfite or sodium sulfite, sodium sulfide, butylated hydroxyanisole, butylated hydroxytoluene, ascorbyl palmitate, propyl gallate and mixtures thereof.

Any other category excipient may be included in the stabilizer list in the present invention pharmaceutical composition. The stabilizers may be present in amount from about 0.01% to about 10% w/w of the composition.

The solvents according to the present invention, but are not limited to, for the purpose of film coating/granulation includes water, methanol, ethanol, acetone, diacetone, polyols, polyethers, oils, esters, alkyl ketones, methylene chloride, isopropyl alcohol, butyl alcohol, methyl acetate, ethyl acetate, isopropyl acetate, castor oil, ethylene glycol monoethyl ether, diethylene glycol monobutyl ether, diethylene glycol monoethyl ether, dimethylsulfoxide, N,N-dimethylformamide, tetrahydrofuran, and any mixtures thereof.

The compositions of the present invention may be coated with one or more film forming materials as known in the art. These coatings may be sugar coatings, film coatings, color coatings, drug coating or the like thereof. The film-forming agents according to the present invention includes, but are not limited to, a water-soluble/water-insoluble film forming polymers, such as hydroxpropyl methylcellulose, methylcellulose, ethylcellulose, hydroxypropyl cellulose, povidone, polydextrose, lactose, maltodextrin, acrylic polymer such as ammonium ethacrylate copolymers, polyvinyl derivative, PVA, PEO, PEG and mixtures thereof. The film coating may optionally contain a plasticizer, such as castor oil, polyethylene glycol, propylene glycol or glycerine, and a coloring or pacifying agent. The film coating may also contain a flavoring and/or sweetening agent to improve palatability.

According to one embodiment, the pharmaceutical composition is present in any one of the form selected from single layer composition, bi-layer composition, multi-layer composition, a tablet in tablet, an in-lay tablet, a capsule or any other alternative modification in the composition as accompanied in the present invention.

The dosage forms herein, e.g., fixed dose combination tablets, can be of any suitable size and shape and the invention is not limited in this regard. For example, the dosage forms may be of triangular, round, rectangular, square, capsule, almond, oval, diamond, biconvex, multi-layered, or have an irregular shape. There may also be letters or characters embossed or printed on the dosage form surface.

In one embodiment of the present invention, a pharmaceutical composition is in form of a single layer tablet comprising Empagliflozin or premix thereof in amount from about 1% to about 14% w/w, Sitagliptin phosphate monohydrate or premix thereof in amount from about 15% to about 72% w/w, one or more diluent(s) in amount from about 5% to about 75% w/w, disintegrant in amount from about 1% to 10% w/w, optionally binder in an amount from about 0.5% to about 5% w/w, lubricant in an amount from about 0.1% to about 3% w/w, glidant in an amount from about 0.1 to about 2%, optionally a stabilizer and optionally film forming substance in an amount from about 1.5% to about 6% w/w of the composition.

In one embodiment of the present invention, a pharmaceutical composition is in form of a single layer tablet comprising Empagliflozin or premix thereof, Sitagliptin phosphate monohydrate or premix thereof, one or more diluent which may include but is not limited to MCC, calcium hydrogen phosphate, lactose, mannitol and starch, one or more disintegrant which may include but is not limited to croscarmellose sodium, sodium starch glycolate, crospovidone, low substituted hydroxypropyl cellulose, optionally one or more binder which may include but is not limited to hydroxypropyl cellulose, hydroxypropyl methyl cellulose, povidone, Copovidone, starch, one or more lubricant which may include but is not limited to magnesium stearate, sodium stearyl fumerate, one or more glidant which may include but is not limited to talc, colloidal silicon dioxide, one or more film forming material which may include but is not limited to Opadry, HPC, HPMC, PVA.

In one aspect of the embodiment, the pharmaceutical composition is a single layer tablet comprising separate granules of Sitagliptin and Empagliflozin, wherein the composition comprises 4.17% Empagliflozin, 18.83% Lactose monohydrate, 6.67% Microcrystalline cellulose, 0.67% Croscarmellose Sodium, 1% HPC, 20.68% Sitagliptin phosphate, 12.02% Microcrystalline cellulose, 20.63% Dibasic calcium phosphate, 1.5% Croscarmellose Sodium, 2% Povidone, 5.83% Microcrystalline cellulose, 1.67% Croscarmellose sodium, 0.33% Anhydrous colloidal silicon dioxide, 1% magnesium stearate, 3% sodium stearyl fumerate, and 3% PVA based coating material.

In one aspect of the embodiment, the pharmaceutical composition is a single layer tablet comprising separate granules of Sitagliptin and Empagliflozin, wherein the composition comprises 25 mg Empagliflozin, 113 mg Lactose monohydrate, 40 mg Microcrystalline cellulose, 4 mg Croscarmellose Sodium, 6 mg HPC, 124.06 mg Sitagliptin phosphate, 72.14 mg Microcrystalline cellulose, 123.8 mg Dibasic calcium phosphate, 9 mg Croscarmellose Sodium, 12 mg Povidone, 35 mg Microcrystalline cellulose, 10 mg Croscarmellose sodium, 2 mg Anhydrous colloidal silicon dioxide, 6 mg magnesium stearate, 18 mg sodium stearyl fumerate and 18 mg PVA based coating material.

In one another embodiment of the present invention, a pharmaceutical composition is in form of a bilayer layer tablet comprising a first layer comprising Empagliflozin or premix thereof in an from about 0.5% to about 10% w/w, one or more diluent(s) in an amount from about 5% to about 40% w/w, a disintegrant in an amount from about 0.1% to about 8% w/w, a binder in an amount from about 0% to about 5% w/w, a lubricant in an amount from about 0.1% to about 4% w/w, a glidant in an amount from about 0.1% to about 2% w/w, a second layer comprising Sitagliptin phosphate monohydrate or premix thereof in amount from about 3% to about 50% w/w, one or more diluent(s) in amount from about 5% to about 40% w/w, disintegrant in amount from about 0.5% to 8% w/w, optionally a binder in amount from about 0.1% to 5% w/w, one or more lubricant(s) in an amount from about 0.5% to about 5% w/w, optionally a stabilizer and a film forming substance in an amount from about 1.5% to about 6% w/w of the composition.

In one another embodiment of the present invention, a pharmaceutical composition is in form of a bilayer layer tablet comprising a first layer comprising Empagliflozin or premix thereof, one or more diluent which may include but is not limited to microcrystalline cellulose, calcium hydrogen phosphate, lactose, mannitol and starch, one or more disintegrant which may include but is not limited to croscarmellose sodium, sodium starch glycolate, crospovidone, low substituted hydroxypropyl cellulose, one or more binder which may include but is not limited to hydroxypropyl cellulose, hydroxypropyl methyl cellulose, povidone, copovidone, starch, one or more lubricant which may include but is not limited to magnesium stearate, sodium stearyl fumerate, one or more glidant which may include but is not limited to talc, colloidal silicon dioxide, and comprises a second layer comprising Sitagliptin phosphate monohydrate or premix thereof, one or more diluent(s) which may include but is not limited to microcrystalline cellulose, calcium hydrogen phosphate, lactose, mannitol and starch, one or more disintegrant which may include but is not limited to croscarmellose sodium, sodium starch glycolate, crospovidone, low substituted hydroxypropyl cellulose, one or more lubricant which may include but is not limited to magnesium stearate, sodium stearyl fumerate, and comprises one or more film forming material which may include but is not limited to Opadry, HPC, HPMC, PVA.

In one aspect of the embodiment, the pharmaceutical composition is a bilayer tablet comprising separate layers of Sitagliptin and Empagliflozin, wherein the Empagliflozin layer comprises 4.17% Empagliflozin, 18.82% Lactose monohydrate, 6.67% Microcrystalline cellulose, 0.167% Croscarmellose Sodium, 0.017% coloring agent, 1.33% HPC, 1.33% Microcrystalline cellulose, 0.33% Croscarmellose Sodium, 0.167% Anhydrous colloidal silicon dioxide and 0.33% magnesium stearate, and the Sitagliptin layer comprises 20.68% Sitagliptin phosphate, 12.02% Microcrystalline cellulose, 20.63% Dibasic calcium phosphate, 1.5% Croscarmellose Sodium, 2% Povidone, 5.5% Microcrystalline cellulose, 1.33% Croscarmellose sodium, 0.33% Anhydrous colloidal silicon dioxide, 0.67% magnesium stearate, 2% sodium stearyl fumerate and 3% PVA based coating material.

In one aspect of the embodiment, the pharmaceutical composition is a bilayer tablet comprising separate layers of Sitagliptin and Empagliflozin, wherein the Empagliflozin layer comprises 25 mg Empagliflozin, 112.9 mg Lactose monohydrate, 40 mg Microcrystalline cellulose, 1 mg Croscarmellose Sodium, 0.1 mg colouring agent, 8 mg HPC, 8 mg Microcrystalline cellulose, 2 mg Croscarmellose Sodium, 1 mg Anhydrous colloidal silicon dioxide and 1 mg magnesium stearate and the Sitagliptin layer comprises 124.06 mg Sitagliptin phosphate, 72.14 mg Microcrystalline cellulose, 123.8 mg Dibasic calcium phosphate, 9 mg Croscarmellose Sodium, 12 mg Povidone, 33 mg Microcrystalline cellulose, 8 mg Croscarmellose sodium, 2 mg Anhydrous colloidal silicon dioxide, 4 mg magnesium stearate, 12 mg sodium stearyl fumarate and 18 mg PVA based coating material.

The pharmaceutical composition of the present invention can be obtained by a known conventional methods like direct compression, wet granulation, dry granulation, roller compaction or slugging, fluidized bed granulation, rapid mixture granulation, solvent evaporation, hot-melt extrusion or like thereof. The wet granulation process may involve shear granulators (such as planetary mixers), high shear mixer granulators (such as Fielder or Diosna), twin screw granulators (such as ConsiGma) and Fluid Bed Granulators (such as Aeromatic or Glatt).

The pharmaceutical composition of the present invention can be preferably packed into blisters or bottles or a like thereof. Preferred blisters are made of material or laminate, which ensures high protection against humidity, oxygen and UV radiation. It is preferred that blisters are made of PVC, OPA, aluminium foil, PCTFE, PVDC, PVDC-coated PVC, PVC/PE/PCTFE laminate, CFF, COC or combination thereof.

The present invention is illustrated below by reference to the following examples.

However, one skilled in the art will appreciate that the specific methods and results discussed are merely illustrative of the invention, and not to be construed as limiting the invention, as many variations thereof are possible without departing from the spirit and scope of the invention.

EXAMPLES

Example 1: Single Layer Tablet of Sitagliptin and Empagliflozin

Single layer tablets of fixed dose combination of Sitagliptin and Empagliflozin were prepared by wet granulation method wherein both Sitagliptin and Empagliflozin were present together in the dry mix.

TABLE 1

Composition of single layer tablets with both drugs present together in the dry mix (mg/tab)

| Ingredients | WG 1 | WG 2 |
|---|---|---|
| Dry Mix | | |
| Empagliflozin | 25.00 | 25.00 |
| Sitagliptin phosphate monohydrate | 124.06 | 124.06 |
| Lactose monohydrate | 148.94 | 159.44 |
| Microcrystalline cellulose (Flocel 101) | 100.00 | 100.00 |
| Croscarmellose sodium | 9.00 | 4.5 |
| Binder Solution | | |
| Hydroxypropylcellulose (Klucel-LF) | 12.00 | 14.00 |
| Purified Water | q.s | q.s |
| Extra Granular Part | | |
| Microcrystalline cellulose (Flocel 102) | 51.00 | 51.00 |
| Croscarmellose sodium | 18.00 | 10.00 |
| Anhydrous colloidal silicon dioxide | 3.00 | 3.00 |
| Magnesium stearate | 4.00 | 4.00 |
| Sodium stearyl fumarate | 15.00 | 15.00 |
| Total weight of uncoated tablet | 510.00 | 510.00 |
| Opadry (PVA Based) | 16.00 | 16.00 |
| Purified Water | q.s | q.s |
| Total weight of coated tablets | 526.00 | 526.00 |

Manufacturing Procedure:

1. Empagliflozin, Sitagliptin phosphate monohydrate, lactose monohydrate, microcrystalline cellulose and croscarmellose sodium were co-sifted through suitable sieve and were loaded in a rapid mixer granulator.

2. Binder solution was prepared by adding hydroxypropyl cellulose (Klucel-LF) in hot purified water under stirring and was allowed to cool to get a clear solution and Dry mix part of step 1 was granulated using prepared binder solution in a rapid mixer granulator.
3. Granules of step 2 were then dried in a fluidized bed dryer to get desired LOD and were sifted through suitable sieve and collected in a polybag.
4. Croscarmellose sodium, anhydrous colloidal silicon dioxide and microcrystalline cellulose were co-sifted through a suitable sieve and were blended with dried granules of step 3 were in a blender for 10 minutes.
5. Magnesium stearate and sodium stearyl fumarate were co-sifted through a suitable sieve and were mixed with blend of step 4 in a blender for 5 minutes.
6. Tablets were compressed using pre-compression blend of step 5 in a compression machine using suitable tooling.
7. Coating dispersion was prepared by dispersing Opadry in purified water under stirring to get a homogenous dispersion and was used to coat the tablets of step 6 in an auto coater.

Example 2: In-Vitro Dissolution of Batches WG 1 & WG 2

The tablets of batches WG 1 and WG 2 were evaluated for in-vitro dissolution study using USP paddle type apparatus in 900 ml of 0.1 N HCl at 50 RPM. As seen from the results, the in-vitro dissolution for Empagliflozin was faster in WG 1, whereas it was similar to and matched to that of the reference product in batch WG 2.

TABLE 2

In-vitro dissolution of WG 1 & WG 2 in 0.1N HCl

| Time | % Drug Release of Sitagliptin | | | % Drug Release of Empagliflozin | | |
|---|---|---|---|---|---|---|
| (Mins) | WG 1 | WG 2 | Ref. | WG 1 | WG 2 | Ref. |
| 5 | 67 | 63 | 64 | 71 | 70 | 73 |
| 10 | 90 | 81 | 81 | 90 | 84 | 87 |
| 15 | 96 | 87 | 87 | 93 | 90 | 92 |
| 20 | 97 | 91 | 89 | 94 | 93 | 94 |
| 30 | 98 | 92 | 90 | 95 | 95 | 95 |
| 45 | 98 | 93 | 91 | 95 | 96 | 96 |
| Infinite | 100 | 99 | 100 | 96 | 98 | 97 |

Example 3: Accelerated Stability Analysis of Batch WG 2

The tablets of batch WG 2 were packed in opaque PVC/PE/PVDC (triplex) blisters and in HDPE bottles and were stored at 40° C./75% RH. The tablets were evaluated at initial and after 1 month for any increase in any known or unknown or total impurities and for other physico-chemical parameters. The results are summarized in table 3. As seen from the results, there was a significant increase in the single max and total impurities for Sitagliptin at the end of 1 month in both the packages. This increase in the impurities could be due to inherent stability issues of DPP-4 inhibitors with a primary or secondary amino group with a number of customary excipients or due to incompatibility with Empagliflozin. Further experimentation were directed to increase the stability of the fixed dose combination by formulating as single layer tablets with separate granules of Empagliflozin and Sitagliptin as well as a bilayer tablet.

TABLE 3

Accelerated stability studies of WG 2

| Parameter | Initial | Triplex | HDPE Bottle |
|---|---|---|---|
| | Tablet | | |
| % Water Content | 4.32% | 4.43% | 4.36% |
| Disintegration time | 65 sec | 47 sec | 52 sec |
| Hardness | 152N | 139N | 127N |
| Average Weight (mg) | 526.22 | 531.73 | 526.46 |
| | Empagliflozin | | |
| Hydroxyl Impurity | ND | ND | ND |
| Diol Impurity | ND | ND | ND |
| Methyl Impurity | ND | ND | ND |
| Bromo Impurity | ND | ND | ND |
| Furanose Impurity | ND | ND | ND |
| Acetyl Impurity | ND | ND | ND |
| Methoxy Impurity | ND | ND | ND |
| Any individual impurity | 0.043 | ND | ND |
| Total Impurities | 0.054 | ND | ND |
| In-vitro dissolution at 30 mins | 92% | 94% | 94% |
| Assay (95%-105%) | 101.80% | 102.72% | 102.68% |
| | Sitagliptin | | |
| Triazol Impurity | ND | ND | ND |
| Acid Impurity | ND | ND | ND |
| Impurity B | ND | 0.007 | 0.007 |
| Impurity C | ND | 0.013 | 0.006 |
| Any individual impurity | 0.175 | 1.341 | 0.819 |
| Total Impurities | 0.175 | 1.399 | 0.839 |
| In-vitro dissolution at 30 mins | 95% | 94% | 94% |
| Assay (95%-105%) | 99.4% | 100.54% | 101.8% |

Example 4: Single Layer Tablet with Intra-Granular Sitagliptin and Extra Granular Empagliflozin Single layer tablets of fixed dose combination of Sitagliptin and Empagliflozin were prepared by wet granulation method wherein Sitagliptin was present in dry mix intra-granularly and Empagliflozin was added extra-granularly. Tablets were prepared similar to the procedure described in example 1 except that Empagliflozin was added extra-granularly.

TABLE 4

| Composition of single layer tablets with intra-granular Sitagliptin and extra-granular Empagliflozin (mg/tab) | |
|---|---|
| Ingredients | WG 3 |
| Dry Mix | |
| Sitagliptin phosphate monohydrate | 124.06 |
| Dibasic calcium phosphate | 123.80 |
| Microcrystalline cellulose (Flocel 101) | 72.14 |
| Croscarmellose sodium | 9.00 |
| Binder Solution | |
| Polyvinylpyrrolidone (PVP K 30) | 12.00 |
| Purified Water | q.s |
| Extra Granular Part | |
| Empagliflozin | 25.00 |
| Lactose monohydrate (Super tab 11 SD) | 52.00 |
| Microcrystalline cellulose (Flocel 102) | 52.00 |
| Croscarmellose sodium | 18.00 |
| Anhydrous colloidal silicon dioxide | 3.00 |
| Magnesium stearate | 4.00 |
| Sodium stearyl fumarate | 15.00 |
| Total weight of uncoated tablet | 510.00 |
| Opadry (PVA Based) | 16.00 |
| Purified Water | q.s |
| Total weight of coated tablets | 526.00 |

Example 5: Single Layer Tablet with Separate Granules of Sitagliptin and Empagliflozin Single layer tablets of fixed dose combination of Sitagliptin and Empagliflozin were prepared by wet granulation method with separate granules of Sitagliptin and Empagliflozin.

TABLE 5

| Composition of single layer tablets with separate granules of Sitagliptin and Empagliflozin (mg/tab) | | |
|---|---|---|
| Ingredients | WG 4 | WG 5 |
| Empagliflozin Granules Dry Mix | | |
| Empagliflozin | 25.00 | 25.00 |
| Lactose monohydrate | 113.00 | 113.00 |
| Microcrystalline cellulose (Flocel 101) | 40.00 | 40.00 |
| Croscarmellose sodium | 4.00 | 4.00 |
| Binder Solution | | |
| Hydroxypropylcellulose (Klucel-LF) | 6.00 | 6.00 |
| Purified Water | q.s | q.s |
| Sitagliptin Granules | | |
| Sitagliptin Phosphate | 124.06 | 124.06 |
| Microcrystalline cellulose (Flocel 102) | 72.14 | 72.14 |
| Dibasic Calcium phosphate (Fine granules) | 123.80 | 123.80 |
| Croscarmellose sodium | 9.00 | — |
| Binder Solution | | |
| Povidone (Kollidone 30 LP) | 12.00 | 12.00 |
| Purified Water | q.s | q.s |
| Extra Granular Part | | |
| Microcrystalline cellulose (Flocel 102) | 35.00 | 35.00 |
| Croscarmellose sodium | 10.00 | 19.00 |

TABLE 5-continued

| Composition of single layer tablets with separate granules of Sitagliptin and Empagliflozin (mg/tab) | | |
|---|---|---|
| Ingredients | WG 4 | WG 5 |
| Anhydrous colloidal silicon dioxide | 2.00 | 2.00 |
| Magnesium stearate | 6.00 | 6.00 |
| Sodium stearyl fumarate | 18.00 | 18.00 |
| Total weight of uncoated tablet | 600.00 | 600.00 |
| Opadry (PVA Based) | 18.00 | 18.00 |
| Purified Water | q.s | q.s |
| Total weight of coated tablets | 618.00 | 618.00 |

Manufacturing Procedure:

1. Empagliflozin, lactose monohydrate, microcrystalline cellulose and croscarmellose sodium were co-sifted through suitable sieve and were loaded in a rapid mixer granulator.
2. Binder solution was prepared by adding hydroxypropyl cellulose (Klucel-LF) in hot purified water under stirring and was allowed to cool to get a clear solution and dry mix part of step 1 was granulated using prepared binder solution in a rapid mixer granulator.
3. Granules of step 2 were then dried in a fluidized bed dryer to get desired LOD and were sifted through suitable sieve and were collected in a polybag.
4. Sitagliptin phosphate monohydrate, microcrystalline cellulose, dibasic calcium phosphate, croscarmellose sodium were co-sifted through suitable sieve and were loaded in a rapid mixer granulator.
5. Binder solution was prepared by adding Povidone (Kollidone 30 LP) in purified water under stirring to get a clear solution and the dry mix part of step 4 was granulated using prepared binder solution in a rapid mixer granulator.
6. Granules of step 5 were then dried in a fluidized bed dryer to get desired LOD and were sifted through suitable sieve and were collected in a polybag.
7. Croscarmellose sodium, anhydrous colloidal silicon dioxide and microcrystalline cellulose were co-sifted through a suitable sieve and were blended with dried granules of step 3 and step 6 in a blender for 10 minutes.
8. Magnesium stearate and sodium stearyl fumarate were co-sifted through a suitable sieve and were mixed with blend of step 7 in a blender for 5 minutes.
9. Tablets were compressed using pre-compression blend of step 8 in a compression machine using suitable tooling.
10. Coating dispersion was prepared by dispersing Opadry in purified water under stirring to get a homogenous dispersion and was used to coat the tablets of step 9 in an auto coater.

Example 6: In-Vitro Dissolution, Content Uniformity & Assay of Batch WG 4

The tablets of batch WG 4 were evaluated for in-vitro dissolution study using USP paddle type apparatus in 900 ml of 0.1 N HCl at 50 RPM. As seen from the results, the in-vitro dissolution for Empagliflozin and Sitagliptin in batch WG 4 was similar to and matched to that of the reference product. The tablets showed optimum content uniformity & assay.

TABLE 6

| In-vitro dissolution of WG 4 in 0.1N HCl | | | | |
|---|---|---|---|---|
| Time | % Drug Release of Empagliflozin | | % Drug Release of Sitagliptin | |
| (Mins) | WG 4 | Ref. | WG 4 | Ref. |
| 5 | 64 | 64 | 70 | 73 |
| 10 | 84 | 81 | 85 | 87 |
| 15 | 91 | 87 | 90 | 92 |
| 20 | 94 | 89 | 92 | 94 |
| 30 | 95 | 90 | 94 | 95 |
| 45 | 96 | 91 | 94 | 96 |
| Infinite | 99 | 100 | 96 | 97 |

TABLE 7

| Content Uniformity & Assay of WG 4 | | |
|---|---|---|
| Result | % Empagliflozin | % Sitagliptin |
| Avg | 100.45 | 99.09 |
| SD | 1.67 | 0.8 |
| % RSD | 1.66 | 0.81 |
| Assay | 101.26 | 98.88 |

Example 7: Accelerated Stability Study of WG 4

The tablets of batch WG 4 were packed in opaque PVC/PE/PVDC (triplex) blisters and in HDPE bottles and were stored at 40° C./75% RH. The tablets were evaluated at initial, after 1 month and after 3 months for any increase in any known or unknown or total impurities and for other physico-chemical parameters. The results are summarized in table 7. As seen from the results, the tablets of batch WG 4 remained stable in both triplex and HDPE bottles. There was no significant increase in any known, unknown or total impurities for Empagliflozin or for Sitagliptin. The in-vitro dissolution, assay, water content, hardness, disintegration time also remained within limits.

TABLE 8

| Accelerated stability studies of WG 4 | | | | | |
|---|---|---|---|---|---|
| | | Triplex | | HDPE Bottle | |
| Parameter | Initial | 1 M | 3 M | 1 M | 3 M |
| Tablet | | | | | |
| Average Weight (mg) | 620.44 | 626.56 | 628.01 | 621.18 | 620.21 |
| Hardness (N) | 155 | 141 | 119 | 126 | 139 |
| Disintegration time (Sec) | 47 Sec | 52 Sec | 60 | 53 | 61 |
| % Water Content | 4.15 | 3.91 | 3.99 | 3.76 | 3.44 |
| Empagliflozin | | | | | |
| Acetyl Impurity | ND | ND | ND | ND | ND |
| Hydroxyl Impurity | ND | ND | ND | ND | ND |
| Diol Impurity | ND | ND | ND | ND | ND |
| Methyl Impurity | ND | ND | ND | ND | ND |
| Bromo Impurity | ND | ND | ND | ND | ND |
| Furanose Impurity | ND | ND | ND | ND | ND |
| Methoxy Impurity | ND | ND | ND | ND | ND |
| Any individual impurity | 0.044 | ND | 0.091 | ND | 0.064 |
| Total Impurities | 0.056 | ND | 0.266 | ND | 0.186 |
| In-vitro dissolution at 30 mins | 95.36 | 93.85 | 92.20 | 94.49 | 97.34 |
| Assay (95%-105%) | 101.26 | 101.32 | 101.02 | 103.59 | 102.61 |

TABLE 8-continued

| Accelerated stability studies of WG 4 | | | | | |
|---|---|---|---|---|---|
| | | Triplex | | HDPE Bottle | |
| Parameter | Initial | 1 M | 3 M | 1 M | 3 M |
| Sitagliptin | | | | | |
| Triazol Impurity | ND | ND | BQL | ND | ND |
| Impurity B | ND | BQL | BQL | BQL | BQL |
| Impurity C | ND | ND | ND | ND | ND |
| Acid Impurity | ND | ND | BQL | ND | ND |
| Any individual impurity | ND | BQL | 0.129 | BQL | BQL |
| Total Impurities | BQL | BQL | 0.129 | BQL | BQL |
| In-vitro dissolution at 30 mins | 93.70 | 93.13 | 92.89 | 92.96 | 95.35 |
| Assay (95%-105%) | 98.88 | 100.44 | 96.91 | 99.80 | 95.80 |

Example 8: Bilayer Tablet of Sitagliptin and Empagliflozin

Bilayer tablets of fixed dose combination of Sitagliptin and Empagliflozin were prepared wherein both layers were prepared by wet granulation method.

TABLE 9

| Composition of bilayer tablets of Sitagliptin and Empagliflozin | | | |
|---|---|---|---|
| Ingredients | WG 6 | WG 7 | WG 8 |
| Empagliflozin Layer Dry Mix | | | |
| Empagliflozin | 25.00 | 25.00 | 25.00 |
| Lactose monohydrate | 113.90 | 112.90 | 112.90 |
| Microcrystalline cellulose (Flocel 101) | 40.00 | 40.00 | 40.00 |
| Iron Oxide Yellow | 0.10 | 0.100 | 0.100 |
| Croscarmellose sodium | 2.00 | 1.00 | 1.00 |
| Binder Solution | | | |
| Hydroxypropylcellulose (Klucel-LF) | 6.00 | 8.00 | 8.00 |
| Purified Water | q.s | q.s | q.s |
| Extra Granular Part | | | |
| Microcrystalline cellulose (Flocel 102) | 8.00 | 8.00 | 8.00 |
| Croscarmellose sodium | 2.00 | 2.00 | 2.00 |
| Anhydrous colloidal silicon dioxide | 1.00 | 1.00 | 1.00 |
| Magnesium stearate | 2.00 | 2.00 | 2.00 |
| Total weight of Empagliflozin Layer | 200.00 | 200.00 | 200.00 |
| Sitagliptin Layer | | | |
| Sitagliptin Phosphate | 124.06 | 124.06 | 124.06 |
| Microcrystalline cellulose (Flocel 102) | 72.14 | 72.14 | 72.14 |
| Dibasic Calcium phosphate (Fine granules) | 123.80 | 123.80 | 123.80 |
| Croscarmellose sodium | 9.00 | 9.00 | — |
| Binder Solution | | | |
| Povidone (Kollidone 30 LP) | 12.00 | 12.00 | 12.00 |
| Purified Water | q.s | q.s | q.s |
| Extra Granular Part | | | |
| Microcrystalline cellulose (Flocel 102) | 33.00 | 33.00 | 33.00 |
| Croscarmellose sodium | 8.00 | 8.00 | 17.00 |

TABLE 9-continued

| Composition of bilayer tablets of Sitagliptin and Empagliflozin | | | |
|---|---|---|---|
| Ingredients | WG 6 | WG 7 | WG 8 |
| Anhydrous colloidal silicon dioxide | 2.00 | 2.00 | 2.00 |
| Magnesium stearate | 4.00 | 4.00 | 4.00 |
| Sodium stearyl fumarate | 12.00 | 12.00 | 12.00 |
| Total weight of Sitagliptin Layer | 400.00 | 400.00 | 400.00 |
| Total weight of uncoated tablet | 600.00 | 600.00 | 600.00 |
| Opadry (PVA Based) | 18.00 | 18.00 | 18.00 |
| Purified Water | q.s | q.s | q.s |
| Total weight of coated tablets | 618.00 | 618.00 | 618.00 |

Manufacturing Procedure:

1. Empagliflozin, lactose monohydrate, microcrystalline cellulose, iron oxide yellow and croscarmellose sodium were co-sifted through suitable sieve and were loaded in a rapid mixer granulator.
2. Binder solution was prepared by adding hydroxypropyl cellulose (Klucel-LF) in hot purified water under stirring and was allowed to cool to get a clear solution and the dry mix part of step 1 was granulated using prepared binder solution in a rapid mixer granulator.
3. Granules of step 3 were then dried in a fluidized bed dryer to get desired LOD and were sifted through suitable sieve and were collected in a polybag.
4. Croscarmellose sodium, anhydrous colloidal silicon dioxide and microcrystalline cellulose were co-sifted through a suitable sieve and were blended with dried granules of step 3 in a blender for 10 minutes.
5. Magnesium stearate was co-sifted through a suitable sieve and were mixed with blend of step 4 in a blender for 5 minutes.
6. Sitagliptin phosphate monohydrate, microcrystalline cellulose, dibasic calcium phosphate, croscarmellose sodium were co-sifted through suitable sieve and were loaded in a rapid mixer granulator.
7. Binder solution was prepared by adding Povidone (Kollidone 30 LP) in purified water under stirring to get a clear solution and the dry mix part of step 6 was granulated using binder solution in a rapid mixer granulator.
8. Granules of step 11 were then dried in a fluidized bed dryer to get desired LOD and were sifted through suitable sieve and were collected in a polybag.
9. Croscarmellose sodium, anhydrous colloidal silicon dioxide and microcrystalline cellulose were co-sifted through a suitable sieve and were blended with dried granules of step 8 in a blender for 10 minutes.
10. Magnesium stearate and sodium stearyl fumarate were co-sifted through a suitable sieve and were mixed with blend of step 9 in a blender for 5 minutes.
11. Bilayer tablets were compressed using pre-compression blend of step 5 and step 10 in a bilayer compression machine using suitable tooling.
12. Coating dispersion was prepared by dispersing Opadry in purified water under stirring to get a homogenous dispersion and the tablets of step 11 were coated with coating dispersion in an auto coater.

Example 9: In-Vitro Dissolution, Content Uniformity & Assay of Batches WG 6& WG7

The tablets of batches WG 6 and WG 7 were evaluated for in-vitro dissolution study using USP paddle type apparatus in 900 ml of 0.1 N HCl at 50 RPM. As seen from the results, the in-vitro dissolution for Empagliflozin was much faster in WG 6, whereas it was similar to and matched to that of the reference product in batch WG 7. The tablets of both the batches showed optimum content uniformity & assay.

TABLE 10

| In-vitro dissolution of WG 6 & WG 7 in 0.1N HCl | | | | | | |
|---|---|---|---|---|---|---|
| Time | % Drug Release of Empagliflozin | | | % Drug Release of Sitagliptin | | |
| (Mins) | WG 6 | WG 7 | Ref. | WG 6 | WG 7 | Ref. |
| 5 | 77 | 70 | 64 | 66 | 78 | 73 |
| 10 | 97 | 89 | 81 | 79 | 88 | 87 |
| 15 | 102 | 95 | 87 | 86 | 92 | 92 |
| 20 | 104 | 96 | 89 | 90 | 94 | 94 |
| 30 | 105 | 97 | 90 | 93 | 95 | 95 |
| 45 | 105 | 98 | 91 | 95 | 96 | 96 |
| Infinite | 106 | 102 | 100 | 98 | 97 | 97 |

TABLE 11

| Content Uniformity & Assay of WG 6 and WG 7 | | | | |
|---|---|---|---|---|
| | WG 6 | | WG 7 | |
| Result | % Empagliflozin | % Sitagliptin | % Empagliflozin | % Sitagliptin |
| Avg | 103.64 | 96.62 | 103.82 | 99.80 |
| SD | 2.48 | 1.06 | 3.43 | 1.90 |
| % RSD | 2.39 | 1.09 | 3.31 | 1.90 |
| Assay | 103.80 | 97.50 | 104.1 | 100.10 |

Example 10: Accelerated Stability Study of WG 7

The bilayer tablets of batch WG 7 were packed in opaque PVC/PE/PVDC (triplex) blisters and in HDPE bottles and were stored at 40° C./75% RH. The tablets were evaluated at initial, after 1 month and after 3 months for any increase in any known or unknown or total impurities and for other physico-chemical parameters. The results are summarized in table 11. As seen from the results, the tablets of batch WG 7 remained stable in both triplex and HDPE bottles. There was no significant increase in any known, unknown or total impurities for Empagliflozin or for Sitagliptin. The in-vitro dissolution, assay, water content, hardness, disintegration time also remained within limits.

TABLE 12

| Accelerated stability studies of WG 7 | | | | | |
|---|---|---|---|---|---|
| | | Triplex | | HDPE Bottle | |
| Parameter | Initial | 1 M | 3 M | 1 M | 3 M |
| Tablet | | | | | |
| Average Weight (mg) | 619.31 | 621.90 | 625.21 | 618.60 | 619.21 |
| Hardness (N) | 156 | 135 | 130 | 144 | 135 |
| Disintegration time (Sec) | 43 | 62 | 38 | 55 | 30 |
| % Water Content | 4.05 | 3.91 | 4.19 | 3.89 | 3.60 |
| Empagliflozin | | | | | |
| Acetyl Impurity | ND | ND | ND | ND | ND |
| Hydroxyl Impurity | ND | ND | ND | ND | ND |
| Diol Impurity | ND | ND | ND | ND | ND |
| Methyl Impurity | ND | ND | ND | ND | ND |
| Bromo Impurity | ND | ND | ND | ND | ND |
| Furanose Impurity | ND | ND | ND | ND | ND |
| Methoxy Impurity | ND | ND | ND | ND | ND |
| Any individual impurity | 0.042 | ND | 0.073 | ND | 0.065 |
| Total Impurities | 0.055 | ND | 0.216 | ND | 0.190 |
| In-vitro dissolution at 30 mins | 97.09 | 94.74 | 90.34 | 99.81 | 98.53 |
| Assay (95%-105%) | 104.09 | 104.84 | 103.28 | 104.47 | 104.64 |
| Sitagliptin | | | | | |
| Triazol Impurity | ND | ND | BQL | ND | ND |
| Impurity B | ND | BQL | BQL | BQL | BQL |
| Impurity C | ND | ND | ND | ND | ND |
| Acid Impurity | ND | ND | BQL | ND | ND |
| Any individual impurity | BQL | BQL | BQL | BQL | BQL |
| Total Impurities | BQL | BQL | BQL | BQL | BQL |
| In-vitro dissolution at 30 mins | 95.35 | 94.21 | 91.39 | 94.62 | 90.68 |
| Assay (95%-105%) | 100.14 | 100.72 | 98.23 | 99.73 | 97.75 |

Example 11: Single Layer Tablet with Separate Granules of Sitagliptin and Empagliflozin and Stabilizer In order to further improve the stability of the tablets and reduce any chances of generation of impurities, a stabilizer was added to the formulation. Single layer tablets of fixed dose combination of Sitagliptin and Empagliflozin were prepared with separate granules of Sitagliptin and Empagliflozin wherein the Sitagliptin granules comprised a pharmaceutically acceptable stabilizer. The tablets were prepared similarly to the process described in example 5.

TABLE 13

| Composition of single layer tablets with stabilizer (mg/tab) | | |
|---|---|---|
| Ingredients | WG 9 | WG 10 |
| Empagliflozin Granules Dry Mix | | |
| Empagliflozin | 25.00 | 25.00 |
| Lactose monohydrate | 113.00 | 113.00 |
| Microcrystalline cellulose (Flocel 101) | 40.00 | 40.00 |
| Croscarmellose sodium | 4.00 | 4.00 |
| Binder Solution | | |
| Hydroxypropylcellulose (Klucel-LF) | 6.00 | 6.00 |
| Purified Water | q.s | q.s |
| Sitagliptin Granules | | |
| Sitagliptin Phosphate | 124.06 | 124.06 |
| Microcrystalline cellulose (Flocel 102) | 71.14 | 66.14 |
| Dibasic Calcium phosphate (Fine granules) | 123.80 | 123.80 |
| Croscarmellose sodium | 9.00 | 9.00 |
| Binder Solution | | |
| Povidone (Kollidone 30 LP) | 12.00 | 12.00 |
| L-arginine | 1.00 | 6.00 |
| Purified Water | q.s | q.s |
| Extra Granular Part | | |
| Microcrystalline cellulose (Flocel 102) | 35.00 | 35.00 |
| Croscarmellose sodium | 10.00 | 10.00 |
| Anhydrous colloidal silicon dioxide | 2.00 | 2.00 |
| Magnesium stearate | 6.00 | 6.00 |
| Sodium stearyl fumarate | 18.00 | 18.00 |
| Total weight of uncoated tablet | 600.00 | 600.00 |
| Opadry (PVA Based) | 18.00 | 18.00 |
| Purified Water | q.s | q.s |
| Total weight of coated tablets | 618.00 | 618.00 |

Example 12: In-Vitro Dissolution, Content Uniformity & Assay of Batches WG 9 & WG 10

The tablets of batches WG 9 and WG 10 were evaluated for in-vitro dissolution study using USP paddle type apparatus in 900 ml of 0.1 N HCl at 50 RPM. As seen from the results, the in-vitro dissolution for Empagliflozin and Sitagliptin in batch WG 9 and WG 10 were similar to and matched to that of the reference products. The tablets of both the batches showed optimum content uniformity & assay.

TABLE 14

| In-vitro dissolution of WG 9 & WG 10 in 0.1N HCl | | | | | | |
|---|---|---|---|---|---|---|
| Time | % Drug Release of Empagliflozin | | | % Drug Release of Sitagliptin | | |
| (Mins) | WG 9 | WG 10 | Ref. | WG 9 | WG 10 | Ref. |
| 5 | 69 | 57 | 64 | 76 | 64 | 73 |
| 10 | 87 | 78 | 81 | 88 | 81 | 87 |
| 15 | 94 | 87 | 87 | 93 | 89 | 92 |
| 20 | 97 | 91 | 89 | 95 | 92 | 94 |
| 30 | 98 | 94 | 90 | 96 | 95 | 95 |
| 45 | 99 | 95 | 91 | 96 | 96 | 96 |
| Infinite | 100 | 99 | 100 | 97 | 97 | 97 |

TABLE 15

| Content Uniformity & Assay of WG 9 and WG 10 | | | | |
|---|---|---|---|---|
| | WG 9 | | WG 10 | |
| Result | % Empagliflozin | % Sitagliptin | % Empagliflozin | % Sitagliptin |
| Avg | 100.50 | 97.52 | 100.50 | 98.69 |
| SD | 1.97 | 1.10 | 2.46 | 1.26 |
| % RSD | 1.96 | 1.13 | 2.45 | 1.28 |
| Assay | 100.60 | 97.90 | 102.00 | 99.60 |

We claim:

1. A stable pharmaceutical composition comprising a combination of Sitagliptin or pharmaceutically acceptable salt or solvate thereof with Empagliflozin or pharmaceutically acceptable salt or solvate thereof and at least one or more pharmaceutically acceptable excipients, wherein the pharmaceutical composition comprises a first portion and a second portion, wherein the first portion comprises Sitagliptin or pharmaceutically acceptable salt or solvate thereof in the form of powder or granules along with one or more pharmaceutically acceptable excipients, and the second portion comprises Empagliflozin or pharmaceutically acceptable salt or solvate thereof in the form of powder or granules along with one or more pharmaceutically acceptable excipients.

2. The stable pharmaceutical composition as claimed in claim 1, wherein the composition is in the form of single layer or bilayer tablet.

3. The stable pharmaceutical composition as claimed in claim 2, wherein the pharmaceutically acceptable excipient is selected from the group consisting of diluent, binder, disintegrant, stabilizer, lubricant, glidant, colouring agent, film coating agent and a combination thereof.

4. The stable pharmaceutical composition as claimed in claim 3, wherein the composition, when stored at 40° C. and 75% relative humidity, contains not more than 0.2% of any known or unknown impurity and not more than 2% of the total impurity for Sitagliptin; and contains not more than 0.5% of any known impurity, not more than 0.2% of any unknown impurity and not more than 2% of total impurity for Empagliflozin.

5. The stable pharmaceutical composition as claimed in claim 1, wherein at least 75% of Sitagliptin and Empagliflozin are released within 30 minutes.

6. The stable pharmaceutical composition as claimed in claim 1, wherein the composition comprises 10-40% w/w Sitagliptin, 1-10% w/w Empagliflozin, 5-80% w/w of diluent, 1-10% w/w of disintegrant, 1-10% w/w binder, 0-10% w/w stabilizer, 0.1-5% lubricant, 0.1-5% w/w glidant and 1-10% w/w of film former of the total weight of the composition.

7. The stable pharmaceutical composition as claimed in claim 6, wherein the stabilizer is selected from the group consisting of acidic agent, alkalizing agent, buffering agent, amino acid, anti-oxidant, and a combination thereof.

8. The stable pharmaceutical composition as claimed in claim 7, wherein the stabilizer is L-Arginine.

* * * * *